(12) United States Patent
Gui et al.

(10) Patent No.: US 10,913,892 B1
(45) Date of Patent: Feb. 9, 2021

(54) METHOD FOR PREPARING RATIOMETRIC FLUORESCENT PROBE FOR MELAMINE BASED ON SILVER NANOCLUSTER COMPLEX

(71) Applicant: Qingdao University, Qingdao (CN)

(72) Inventors: Rijun Gui, Qingdao (CN); Yongxin Fu, Qingdao (CN); Hui Jin, Qingdao (CN); Xiangning Bu, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 16/612,416

(22) PCT Filed: Mar. 5, 2019

(86) PCT No.: PCT/CN2019/076942
§ 371 (c)(1),
(2) Date: Nov. 11, 2019

(87) PCT Pub. No.: WO2019/237769
PCT Pub. Date: Dec. 19, 2019

(30) Foreign Application Priority Data

Jun. 13, 2018 (CN) .......................... 2018 1 0604913

(51) Int. Cl.
  *C09K 11/06* (2006.01)
  *C07D 311/78* (2006.01)
  (Continued)

(52) U.S. Cl.
  CPC ............ *C09K 11/06* (2013.01); *C07D 311/78* (2013.01); *C09K 11/58* (2013.01); *G01N 21/643* (2013.01);
  (Continued)

(58) Field of Classification Search
  CPC ........ C09K 11/06; C09K 11/58; C07D 311/78
  See application file for complete search history.

(56) References Cited

U.S. PATENT DOCUMENTS

2011/0207231 A1* 8/2011 Natan .................. G01N 21/658
  436/98

FOREIGN PATENT DOCUMENTS

| CN | 103602670 A | 2/2014 |
|---|---|---|
| CN | 104611416 A | 5/2015 |

(Continued)

OTHER PUBLICATIONS

Fu Yongxin, et al. Melamine-Induced Decomposition and Anti-Fret Effect From a Self-Assembled Complex of Rhodamine 6G and DNA-Stabilized Silver Nanoclusters Used for Dual-Emitting Ratiometric and Naked-Eye-Visible Fluorescence Detection, J. Agric. Food Chem. 2018, 9819-9827, 66.

(Continued)

*Primary Examiner* — Hugh Maupin
(74) *Attorney, Agent, or Firm* — Bayramoglu Law Offices LLC (57) ABSTRACT

A method for preparing a ratiometric fluorescent probe for melamine based on a DNA-stable silver nanocluster-rhodamine 6G complex, wherein the electrostatic self-assembly technology is adopted to construct a silver nanocluster-rhodamine 6G complex. The melamine forms a strong hydrogen bond with thymine in the DNA of the surface of the silver nanocluster, causing rhodamine 6G to dissociate from the surface of the silver nanocluster, destroying the fluorescence resonance energy transfer, so as to restore the fluorescence of the silver nanocluster. This process has little effect on Rhodamine 6G fluorescence which can be used as a reference signal, while silver nanocluster fluorescence can be used as a response signal. By fitting the linear relationship between the ratio of fluorescence emission peak intensities of the silver nanocluster to rhodamine 6G and the molar concentration of the melamine, the ratiometric fluorescent probe for melamine can be constructed.

1 Claim, 2 Drawing Sheets

(51) Int. Cl.
*C09K 11/58* (2006.01)
*G01N 21/64* (2006.01)

(52) U.S. Cl.
CPC ............ *C09K 2211/1007* (2013.01); *C09K 2211/1029* (2013.01); *G01N 2021/6432* (2013.01)

(56) References Cited

FOREIGN PATENT DOCUMENTS

| | | |
|---|---|---|
| CN | 105158225 A | 12/2015 |
| CN | 105334258 A | 2/2016 |
| CN | 106018366 A | 10/2016 |
| CN | 108641708 A | 10/2018 |

OTHER PUBLICATIONS

Han Shuang, et al. Oligonucleotide-Stabilized Fluorescent Silver Nanoclusters for Turn-on Detection of Melamine, Biosensors and Bioelectronics, 2012, 267-270,36.
Hu Jingqiu, et al. Dye-Capped Gold Nanoclusters: Photoinduced Morphological Changes in Gold/Rhodamine 6G Nanoassemblies, J. Phys. Chem. B, 2000, 11103-11109, 104.
Wu Qiongqiong, et al. An Upconversion Fluorescence Resonance Energy Transfer Nanosensor for One Step Detection of Melamine in Raw Milk, Talanta, 2015, 47-53, 136.
Kalaiyarasan Gopi, et al. Melamine Dependent Fluorescence of Glutathione Protected Gold Nanoclusters and Ratiometric Quantification of Melamine in Commercial Cow Milk and Infant Formula, Applied Surface Science, 2017, 963-969, 420.

* cited by examiner

FIG. 4

METHOD FOR PREPARING RATIOMETRIC FLUORESCENT PROBE FOR MELAMINE BASED ON SILVER NANOCLUSTER COMPLEX

CROSS REFERENCE TO THE RELATED APPLICATIONS

This application is the national phase entry of International Application No. PCT/CN2019/076942, filed on Mar. 5, 2019, which is based upon and claims priority to Chinese Patent Application No. 201810604913.2, filed on Jun. 13, 2018, the entire contents of which are incorporated herein by reference.

TECHNICAL FIELD

The present disclosure belongs to the technical field of preparations of noble metal nanomaterials and ratiometric fluorescent probes, and more specifically relates to a method for preparing a ratiometric fluorescent probe for melamine based on a DNA-stable silver nanocluster-rhodamine 6G complex and the probe prepared by the method can be used for a high sensitivity detection of melamine.

BACKGROUND

Melamine, a heterocyclic organic compound containing nitrogen with a nitrogen content of up to 66%, is commonly used in plastics, pesticides, fertilizers and other industries. Adding 1% of melamine can increase a protein content by more than 4% in food, and some companies use melamine to replace protein for high profits. The U.S. Food and Drug Administration and Ministry of Health of the People's Republic of China stipulate a safety limit of 1 mg/kg for infant food and 2.5 mg/kg for adult food. Detecting the content of melamine in food is important for the health of consumer. Present methods of detecting melamine include high performance liquid chromatography, gas chromatography and mass spectrometry, spectrophotometry, surface enhanced Raman scattering and so on. These traditional detection methods generally have problems such as time consumption during sample preparation, complex operation, expensive instrumentation, and high detection cost. Therefore, developing a low-cost, simple, fast and efficient method for detecting melamine has become a key technical object to be attained urgently.

Fluorimetry is an analytical method for substance identification and content determination based on a change of fluorescence intensity or spectral line position caused by reaction of substances or their surface modified functional groups with substances for performing a detection. The method has the advantages of simple operation and high sensitivity. Literatures are searched as follows. Wu et al. used fluorescence resonance energy transfer between up-conversion nanoparticles and gold nanoparticles to detect melamine (An upconversion fluorescence resonance energy transfer nanosensor for one step detection of melamine in raw milk, Qiongqiong Wu, Qian Long, Haitao Li, Youyu Zhang, Shouzhuo Yao, *Talanta*, 2015, 136, 47-53). Kalaiyarasa et al. designed a melamine fluorescence sensor based on gold nanoclusters (Melamine dependent fluorescence of glutathione protected gold nanoclusters and ratiometric quantification of melamine in commercial cow milk and infant formula, Gopi Kalaiyarasan, Anusuya K, James Joseph, *Appl. Surf Sci.*, 2017, 420, 963-969). Cuifeng Jiang et al. reported a method for detecting melamine based on two-photon excitation fluorescence (Patent Publication No. CN105158225A).

Ratiometric fluorescence method is a method of quantitative detection based on a ratio of fluorescence intensities at two different wavelengths by a reaction of dual-emission fluorescent probe with a substance to be detected. Ratiometric fluorescence method has a self-calibration function, which can eliminate a fluorescence interference generated by the system itself and environmental factors, and effectively improve the accuracy and reliability of the detection result of a target object. Silver nanoclusters have unique physicochemical properties, such as strong fluorescence emission, good photostability, high biocompatibility, and sub-nano size, and can be used in nanomedicine, bioimaging, drug delivery, biochemical sensing and many other fields. Rhodamine 6G is a widely used organic dye with the advantages of high photostability, pH insensitivity and high fluorescence quantum yield. Although the literature on melamine fluorescence detection has been reported, the present inventors have first constructed a dual-emission fluorescent probe based on a DNA-stable silver nanocluster-rhodamine 6G complex, and applied the dual-emission fluorescent probe to a ratiometric fluorescence detection of melamine in actual samples. So far, the ratiometric fluorescent probe for melamine based on DNA-stable silver nanocluster-rhodamine 6G complex has not yet been reported in domestic and foreign literature or patent.

SUMMARY

The objective of the present disclosure is to overcome the deficiencies of the prior art described above, and to design a ratiometric fluorescent probe for melamine based on a DNA-stable silver nanocluster-rhodamine 6G complex, where the ratiometric fluorescent probe is simple, easy to prepare, low in cost and high in sensitivity.

In order to achieve the aforementioned objective, the present disclosure provides a method for preparing a ratiometric fluorescent probe for melamine based on a silver nanocluster complex, and a preparation process thereof includes the following steps.

(1) Preparation of DNA-stable silver nanoclusters: at 0° C., adding a certain amount of silver nitrate solution and DNA solution to 1 mL of double-distilled water, stirring magnetically for 20 minutes to form a homogeneous mixture, then adding a freshly prepared sodium borohydride solution, and reacting under a vigorous stirring in a dark place for 20 minutes. The resulting product solution is filtered by a 0.4 μm filter, and a filtrate is dialyzed through a dialysis bag with a molecular weight cut-off of 5000 Daltons to remove unreacted experimental materials. The solution in the dialysis bag is subjected to a rotary evaporation to remove 90% of the solvent, and then freeze-dried to obtain a dry sample of the silver nanoclusters. The dry sample of the silver nanoclusters is stored at 4° C. in a dark condition.

(2) Preparation of silver nanocluster-rhodamine 6G complex: dissolving the silver nanoclusters prepared in step (1) in 200 μL of double-distilled water, adding 100 μL of citrate buffer to mix well, and then adding 100 μL of rhodamine 6G solution with different concentrations. The mixed solution reacts in a dark place for 30 minutes, and the product solution is subjected to centrifugal separation, ethanol washing and vacuum drying to obtain the silver nanocluster-rhodamine 6G complex.

(3) Dispersing the complex prepared in step (2) in 100 μL of citrate buffer, incubating in a dark place for 30 minutes, measuring fluorescence emission spectra of homogeneous solution of complex corresponding to different molar concentrations of the rhodamine 6G, optimizing the intensity of the double emission fluorescence peak to determine the ratio of silver nanoclusters and rhodamine 6G.

(4) At room temperature and under a slow magnetic stirring, adding 15 μL of melamine solutions with different concentrations to a homogeneous solution of optimized ratio complex prepared in step (3), continuing to stir for 5 minutes to fully react to form a homogeneous solution of the complex and the melamine, measuring fluorescence emission spectra of the homogeneous solution of the complex and melamine corresponding to different molar concentrations of melamine, fitting linear relationship between the ratio of the fluorescence emission peak intensities of the silver nanoclusters to the rhodamine 6G and the molar concentration of the melamine, constructing the ratiometric fluorescent probe for melamine.

In step (1) of the present disclosure, the size of the silver nanocluster is 6-12 nm, and molar concentrations of the silver nitrate, the DNA and the sodium borohydride are 5-10 mmol/L, 200-600 μmol/L and 5-10 mmol/L, respectively. In step (2), pH of the citrate buffer is 5.5-6.5, and the molar concentration of rhodamine 6G is 0.1-2 nmol/L. In step (3), the mass concentration of the complex solution is 1-5 mg/mL. In step (4), the concentration range of the melamine is 0.5-15 mol/L, and the detection limit is 0.05-0.2 mol/L.

Compared with the prior art, the present disclosure employs an electrostatic self-assembly technology to construct a DNA-stable silver nanocluster-rhodamine 6G complex. The absorption spectrum of rhodamine 6G partially overlaps with the fluorescence emission spectrum of silver nanocluster, the fluorescence resonance energy transfer occurs between the two and causes the fluorescence quenching of silver nanocluster, while the fluorescence of rhodamine 6G is enhanced. The added melamine can form a strong hydrogen bond with thymine on the surface of the DNA-stable silver nanocluster, causing rhodamine 6G to dissociate from the surface of the silver nanocluster, increasing the distance between the donor and the receptor, and weakening the fluorescence resonance energy transfer, so as to restore the fluorescence of the silver nanocluster. This process has little effect on Rhodamine 6G fluorescence which can be used as a reference signal, while silver nanocluster fluorescence can be used as a response signal. By fitting the linear relationship between the ratio of the fluorescence emission peak intensities of the silver nanocluster to the rhodamine 6G and the molar concentration of the melamine, the ratiometric fluorescent probe for melamine can be constructed. The probe has simple preparation process, low cost and high product sensitivity, and can be developed into a novel ratiometric fluorescent probe for melamine, where the novel ratiometric fluorescent probe is suitable for efficiently detecting melamine in actual samples.

DETAILED DESCRIPTION OF THE EMBODIMENTS

The present disclosure will be further described below in conjunction with the drawings and specific embodiments.

Embodiment 1

Figure 1:
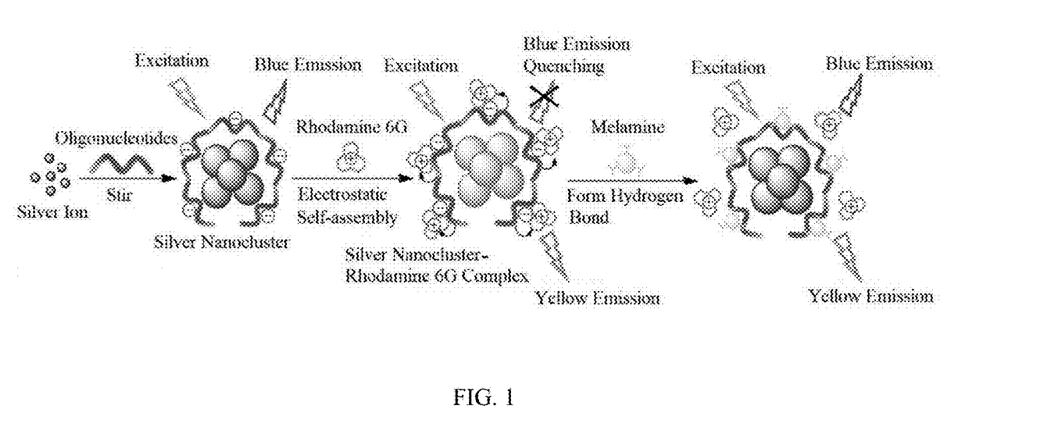
FIG. 1 is a schematic diagram of a method for preparing ratiometric fluorescent probe for melamine based on a DNA-stable silver nanocluster-rhodamine 6G complex in the present disclosure.

This embodiment relates to a method for preparing a ratiometric fluorescent probe for melamine based on a DNA-stable silver nanocluster-rhodamine 6G complex. The preparation process of the ratiometric fluorescent probe for melamine and the principle of the ratiometric fluorescence detection of melamine are shown in FIG. 1, and the specific process steps are as follows:

Preparation of DNA-stable silver nanoclusters: at 0° C., a certain amount of silver nitrate solution and DNA solution are added to 1 mL of double-distilled water, a magnetic stirring is performed for 20 minutes to form a homogeneous mixture, then a freshly prepared sodium borohydride solution is added, and a reaction is carried under a vigorous stirring in a dark place for 20 minutes, wherein molar concentrations of the silver nitrate, the DNA and the sodium borohydride are 5 mmol/L, 200 μL mol/L and 5 mmol/L, respectively. The resulting product solution is filtered by a 0.4 μm filter, and a filtrate is dialyzed through a dialysis bag with a molecular weight cut-off of 5000 Daltons to remove unreacted experimental materials, and the solution in the dialysis bag is subjected to a rotary evaporation to remove 90% of the solvent, and then freeze-dried to obtain a dry sample of the silver nanoclusters, and the dry sample of the silver nanoclusters is stored at 4° C. in a dark condition.

Preparation of silver nanocluster-rhodamine 6G complex: the prepared silver nanoclusters are dissolved in 200 μL of double-distilled water, 100 μL of citrate buffer (pH 5.5) is added to mix well, and then 100 μL of rhodamine 6G solution (0.1-0.5 nmol/L) is added. The mixed solution reacts in a dark place for 30 minutes, and the product solution is subjected to centrifugal separation, ethanol washing and vacuum drying to obtain the silver nanocluster-rhodamine 6G complex.

Figure 2:
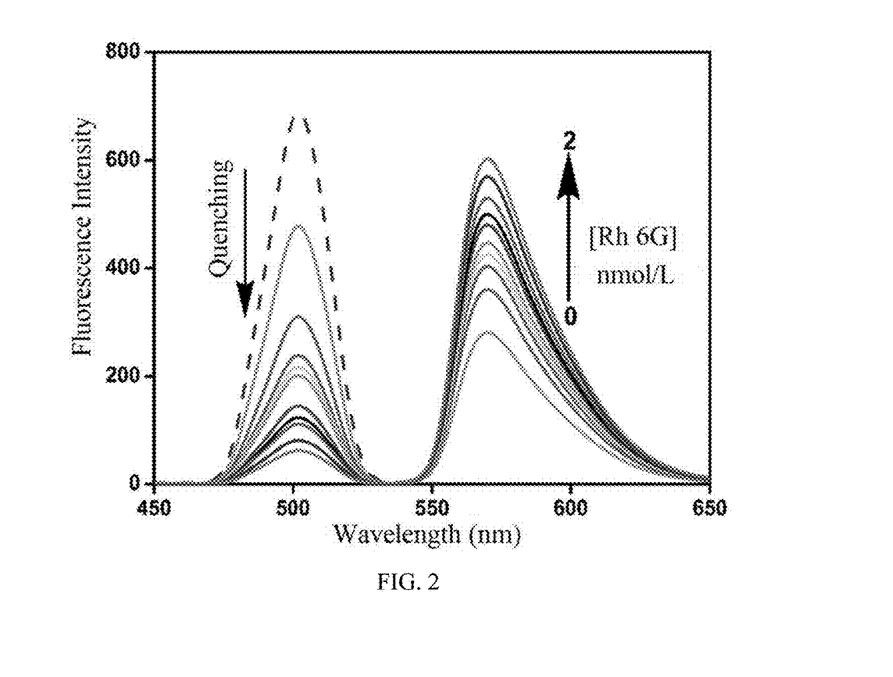
FIG. 2 is a graph showing response to fluorescence emission peak intensity of DNA-stable silver nanocluster-rhodamine 6G complex as molar concentration of rhodamine 6G increases.

The prepared complex is dispersed in 100 μL of citrate buffer, and the mass concentration of the complex is 1-2 mg/mL. After homogeneous solution of the complex is incubated in a dark place for 30 minutes, fluorescence emission spectra of the homogeneous solution of the complex corresponding to different molar concentrations of rhodamine 6G are measured respectively, and the intensity of double emission fluorescence peak is optimized to determine the ratio of silver nanocluster and rhodamine 6G (see FIG. 2).

Figure 3:
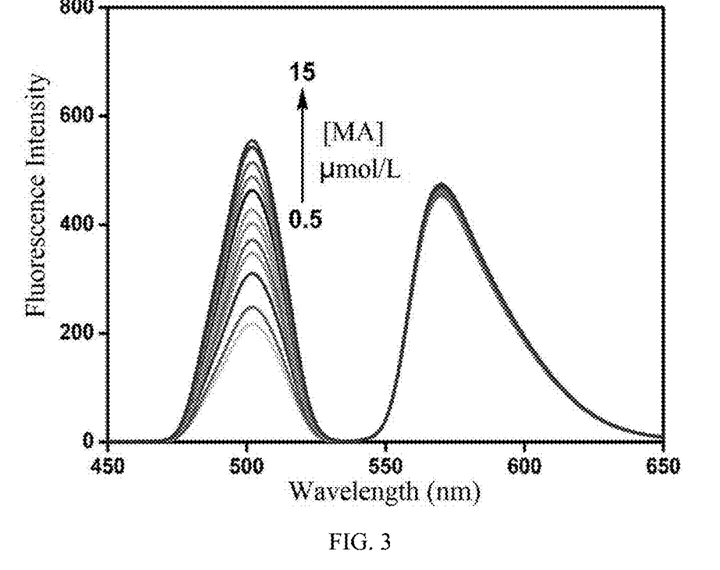
FIG. 3 is a graph showing response to fluorescence emission peak intensity of DNA-stable silver nanocluster-rhodamine 6G complex as molar concentration of melamine increases.
Figure 4:
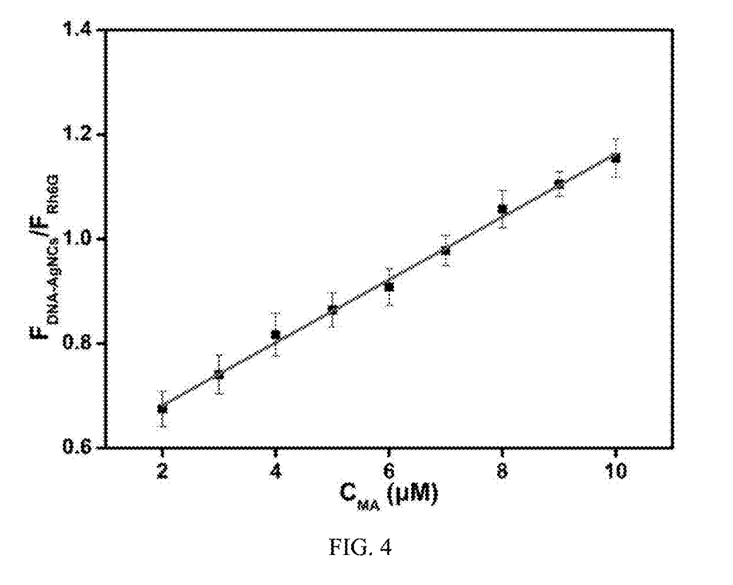
FIG. 4 is a graph showing a fitted linear relationship between the ratio of fluorescence emission peak intensities of DNA-stable silver nanocluster to rhodamine 6G and molar concentration of melamine.

At room temperature and under a slow magnetic stirring, 15 μL of melamine solutions with different concentrations are added to the prepared homogeneous solution of complex having the optimized ratio, and the solution is continuously stirred for 5 minutes to fully react to form a homogeneous solution of the complex and the melamine. Fluorescence emission spectra of the homogeneous solution of the complex and melamine corresponding to different molar concentrations of melamine are measured respectively (see FIG. 3). The ratio $F_{DNA-Ag\ NCs}/F_{Rh\ 6G}$ of fluorescence emission peak intensities of the silver nanocluster to rhodamine 6G and the molar concentration $C_{MA}$ of the melamine are fitted to obtain a linear relationship as $F_{DNA-Ag\ NCs}/F_{Rh\ 6G}=0.06014C_{MA}+0.5612$ ($R^2=0.9959$) (see FIG. 4). Therefore, the ratiometric fluorescent probe for melamine can be constructed, wherein the linear concentration of melamine to be detected is 2-10 μmol/L, and the detection limit of melamine is 0.2 μmol/L.

Embodiment 2

The specific process steps for preparing DNA-stable silver nanoclusters in this embodiment are the same as those in embodiment 1, wherein the molar concentrations of silver nitrate, DNA and sodium borohydride are 8 mmol/L, 400 μmol/L and 7 mmol/L, respectively. The prepared silver nanoclusters are dissolved in 200 μL of double-distilled water, 100 μL of citrate buffer (pH 6.0) is added to mix well, and then 100 μL of rhodamine 6G solution (0.2-1 nmol/L) is added. The mixed solution reacts in a dark place for 30 minutes, and the product solution is subjected to centrifugal separation, ethanol washing and vacuum drying to obtain a silver nanocluster-rhodamine 6G complex. The prepared complex is dispersed in 100 μL of citrate buffer, and the mass concentration of the complex is 1-4 mg/mL. After the homogeneous solution of the complex is incubated in a dark place for 30 minutes, fluorescence emission spectra of the homogeneous solution of the complex corresponding to different molar concentrations of rhodamine 6G are measured respectively, and the intensity of double emission fluorescence peak is optimized to determine the ratio of silver nanocluster and rhodamine 6G. At room temperature and under a slow magnetic stirring, 15 μL of melamine solutions with different concentrations are added to the prepared homogeneous solution of complex having the optimized ratio, and the solution is continuously stirred for 5 minutes to fully react to form a homogeneous solution of the complex and the melamine. Fluorescence emission spectra of the homogeneous solution of the complex and melamine corresponding to different molar concentrations of melamine are measured respectively. By fitting a linear relationship between the ratio of fluorescence emission peak intensities of the silver nanocluster to rhodamine 6G and the molar concentration of the melamine, the ratiometric fluorescent probe for melamine can be constructed, wherein the linear concentration of melamine to be detected is 0.5-10 μmol/L, and the detection limit of melamine is 0.05 μmol/L.

Embodiment 3

The specific process steps for preparing DNA-stable silver nanoclusters in this embodiment are the same as those in embodiment 1, wherein the molar concentrations of silver nitrate, DNA and sodium borohydride are 10 mmol/L, 600 μmol/L and 10 mmol/L, respectively. The prepared silver nanoclusters are dissolved in 200 μL of double-distilled water, 100 μL of citrate buffer (pH 6.5) is added to mix well, and then 100 μL of rhodamine 6G solution (0.2-2 nmol/L) is added. The mixed solution reacts in a dark place for 30 minutes, and the product solution is subjected to centrifugal separation, ethanol washing and vacuum drying to obtain a silver nanocluster-rhodamine 6G complex. The prepared complex is dispersed in 100 μL of citrate buffer, and the mass concentration of the complex is 2-5 mg/mL. After the homogeneous solution of the complex is incubated in a dark place for 30 minutes, fluorescence emission spectra of the homogeneous solution of the complex corresponding to different molar concentrations of rhodamine 6G are measured respectively, and the intensity of double emission fluorescence peak is optimized to determine the ratio of silver nanocluster and rhodamine 6G. At room temperature and under a slow magnetic stirring, 15 μL of melamine solutions with different concentrations are added to the prepared homogeneous solution of complex having the optimized ratio, and the solution is continues stirred for 5 minutes to fully react to form a homogeneous solution of the complex and the melamine. Fluorescence emission spectra of the homogeneous solution of the complex and the melamine corresponding to different molar concentrations of melamine are measured respectively. By fitting a linear relationship between the ratio of fluorescence emission peak intensities of the silver nanocluster to rhodamine 6G and the molar concentration of the melamine, the ratiometric fluorescent probe for melamine can be constructed, wherein the linear concentration of melamine to be detected is 2-15 μmol/L, and the detection limit of melamine is 0.1 μmol/L.

Embodiment 4

This embodiment relates to an application of the ratiometric fluorescent probe for melamine prepared in embodiment 1 in detecting melamine in an actual sample such as milk. The milk is mixed with melamine with different concentrations and acetonitrile, and after 30 minutes of ultrasonic treatment, the mixed solution is obtained. The mixed solution is centrifuged for 15 minutes at a speed of 14000 rpm, and the supernatant is taken and filtered. The filtrate is further diluted 25 times and collected for further detection. Specifically, for melamine, the detection range of molar concentration is 0.5-15 μmol/L, the detection limit is 0.09 μmol/L, detection recovery rate is 99.8-100.5%, and relative standard deviation is 1.1-2.1%. Compared with the prior art, the previous literatures (*Talanta*, 2015, 136, 47-53 and *Appl. Surf Sci.*, 2017, 420, 963-969) use single method or ratiometric fluorescence method to detect melamine, and the detection recovery rate of melamine in milk samples is 94.0-102.0%, and the relative standard deviation is 1.2-3.2%. The ratiometric fluorescent probe of the present disclosure has high detection recovery rate, low relative standard deviation, simple preparation process, low cost and high product sensitivity, and can be developed into a novel ratiometric fluorescent probe for melamine, where the novel ratiometric fluorescent probe is suitable for efficiently detecting melamine in different actual samples.

CROSS REFERENCE TO THE RELATED APPLICATIONS

This application is the national phase entry of International Application No. PCT/CN2019/076942, filed on Mar. 5, 2019, which is based upon and claims priority to Chinese Patent Application No. 201810604913.2, filed on Jun. 13, 2018, the entire contents of which are incorporated herein by reference.

TECHNICAL FIELD

The present disclosure belongs to the technical field of preparations of noble metal nanomaterials and ratiometric fluorescent probes, and more specifically relates to a method for preparing a ratiometric fluorescent probe for melamine based on a DNA-stable silver nanocluster-rhodamine 6G complex and the probe prepared by the method can be used for a high sensitivity detection of melamine.

BACKGROUND

Melamine, a heterocyclic organic compound containing nitrogen with a nitrogen content of up to 66%, is commonly used in plastics, pesticides, fertilizers and other industries. Adding 1% of melamine can increase a protein content by more than 4% in food, and some companies use melamine to replace protein for high profits. The U.S. Food and Drug Administration and Ministry of Health of the People's Republic of China stipulate a safety limit of 1 mg/kg for infant food and 2.5 mg/kg for adult food. Detecting the content of melamine in food is important for the health of consumer. Present methods of detecting melamine include high performance liquid chromatography, gas chromatography and mass spectrometry, spectrophotometry, surface enhanced Raman scattering and so on. These traditional detection methods generally have problems such as time consumption during sample preparation, complex operation, expensive instrumentation, and high detection cost. Therefore, developing a low-cost, simple, fast and efficient method for detecting melamine has become a key technical object to be attained urgently.

Fluorimetry is an analytical method for substance identification and content determination based on a change of fluorescence intensity or spectral line position caused by reaction of substances or their surface modified functional groups with substances for performing a detection. The method has the advantages of simple operation and high sensitivity. Literatures are searched as follows. Wu et al. used fluorescence resonance energy transfer between up-conversion nanoparticles and gold nanoparticles to detect melamine (An upconversion fluorescence resonance energy transfer nanosensor for one step detection of melamine in raw milk, Qiongqiong Wu, Qian Long, Haitao Li, Youyu Zhang, Shouzhuo Yao, *Talanta*, 2015, 136, 47-53). Kalaiyarasa et al. designed a melamine fluorescence sensor based on gold nanoclusters (Melamine dependent fluorescence of glutathione protected gold nanoclusters and ratiometric quantification of melamine in commercial cow milk and infant formula, Gopi Kalaiyarasan, Anusuya K, James Joseph, *Appl. Surf Sci.*, 2017, 420, 963-969). Cuifeng Jiang et al. reported a method for detecting melamine based on two-photon excitation fluorescence (Patent Publication No. CN105158225A).

Ratiometric fluorescence method is a method of quantitative detection based on a ratio of fluorescence intensities at two different wavelengths by a reaction of dual-emission fluorescent probe with a substance to be detected. Ratiometric fluorescence method has a self-calibration function, which can eliminate a fluorescence interference generated by the system itself and environmental factors, and effectively improve the accuracy and reliability of the detection result of a target object. Silver nanoclusters have unique physicochemical properties, such as strong fluorescence emission, good photostability, high biocompatibility, and sub-nano size, and can be used in nanomedicine, bioimaging, drug delivery, biochemical sensing and many other fields. Rhodamine 6G is a widely used organic dye with the advantages of high photostability, pH insensitivity and high fluorescence quantum yield. Although the literature on melamine fluorescence detection has been reported, the present inventors have first constructed a dual-emission fluorescent probe based on a DNA-stable silver nanocluster-rhodamine 6G complex, and applied the dual-emission fluorescent probe to a ratiometric fluorescence detection of melamine in actual samples. So far, the ratiometric fluorescent probe for melamine based on DNA-stable silver nanocluster-rhodamine 6G complex has not yet been reported in domestic and foreign literature or patent.

SUMMARY

The objective of the present disclosure is to overcome the deficiencies of the prior art described above, and to design a ratiometric fluorescent probe for melamine based on a DNA-stable silver nanocluster-rhodamine 6G complex, where the ratiometric fluorescent probe is simple, easy to prepare, low in cost and high in sensitivity.

In order to achieve the aforementioned objective, the present disclosure provides a method for preparing a ratiometric fluorescent probe for melamine based on a silver nanocluster complex, and a preparation process thereof includes the following steps.

(1) Preparation of DNA-stable silver nanoclusters: at 0° C., adding a certain amount of silver nitrate solution and DNA solution to 1 mL of double-distilled water, stirring magnetically for 20 minutes to form a homogeneous mixture, then adding a freshly prepared sodium borohydride solution, and reacting under a vigorous stirring in a dark place for 20 minutes. The resulting product solution is filtered by a 0.4 μm filter, and a filtrate is dialyzed through a dialysis bag with a molecular weight cut-off of 5000 Daltons to remove unreacted experimental materials. The solution in the dialysis bag is subjected to a rotary evaporation to remove 90% of the solvent, and then freeze-dried to obtain a dry sample of the silver nanoclusters. The dry sample of the silver nanoclusters is stored at 4° C. in a dark condition.

(2) Preparation of silver nanocluster-rhodamine 6G complex: dissolving the silver nanoclusters prepared in step (1) in 200 μL of double-distilled water, adding 100 μL of citrate buffer to mix well, and then adding 100 μL of rhodamine 6G solution with different concentrations. The mixed solution reacts in a dark place for 30 minutes, and the product solution is subjected to centrifugal separation, ethanol washing and vacuum drying to obtain the silver nanocluster-rhodamine 6G complex.

(3) Dispersing the complex prepared in step (2) in 100 μL of citrate buffer, incubating in a dark place for 30 minutes, measuring fluorescence emission spectra of homogeneous solution of complex corresponding to different molar concentrations of the rhodamine 6G, optimizing the intensity of the double emission fluorescence peak to determine the ratio of silver nanoclusters and rhodamine 6G.

(4) At room temperature and under a slow magnetic stirring, adding 15 μL of melamine solutions with different concentrations to a homogeneous solution of optimized ratio complex prepared in step (3), continuing to stir for 5 minutes to fully react to form a homogeneous solution of the complex and the melamine, measuring fluorescence emission spectra of the homogeneous solution of the complex and melamine corresponding to different molar concentrations of melamine, fitting linear relationship between the ratio of the fluorescence emission peak intensities of the silver nanoclusters to the rhodamine 6G and the molar concentration of the melamine, constructing the ratiometric fluorescent probe for melamine.

In step (1) of the present disclosure, the size of the silver nanocluster is 6-12 nm, and molar concentrations of the silver nitrate, the DNA and the sodium borohydride are 5-10 mmol/L, 200-600 μmol/L and 5-10 mmol/L, respectively. In step (2), pH of the citrate buffer is 5.5-6.5, and the molar concentration of rhodamine 6G is 0.1-2 nmol/L. In step (3), the mass concentration of the complex solution is 1-5 mg/mL. In step (4), the concentration range of the melamine is 0.5-15 mol/L, and the detection limit is 0.05-0.2 mol/L.

Compared with the prior art, the present disclosure employs an electrostatic self-assembly technology to construct a DNA-stable silver nanocluster-rhodamine 6G complex. The absorption spectrum of rhodamine 6G partially overlaps with the fluorescence emission spectrum of silver nanocluster, the fluorescence resonance energy transfer occurs between the two and causes the fluorescence quenching of silver nanocluster, while the fluorescence of rhodamine 6G is enhanced. The added melamine can form a strong hydrogen bond with thymine on the surface of the DNA-stable silver nanocluster, causing rhodamine 6G to dissociate from the surface of the silver nanocluster, increasing the distance between the donor and the receptor, and weakening the fluorescence resonance energy transfer, so as to restore the fluorescence of the silver nanocluster. This process has little effect on Rhodamine 6G fluorescence which can be used as a reference signal, while silver nanocluster fluorescence can be used as a response signal. By fitting the linear relationship between the ratio of the fluorescence emission peak intensities of the silver nanocluster to the rhodamine 6G and the molar concentration of the melamine, the ratiometric fluorescent probe for melamine can be constructed. The probe has simple preparation process, low cost and high product sensitivity, and can be developed into a novel ratiometric fluorescent probe for melamine, where the novel ratiometric fluorescent probe is suitable for efficiently detecting melamine in actual samples.

DETAILED DESCRIPTION OF THE EMBODIMENTS

The present disclosure will be further described below in conjunction with the drawings and specific embodiments.

Embodiment 1

This embodiment relates to a method for preparing a ratiometric fluorescent probe for melamine based on a DNA-stable silver nanocluster-rhodamine 6G complex. The preparation process of the ratiometric fluorescent probe for melamine and the principle of the ratiometric fluorescence detection of melamine are shown in FIG. 1, and the specific process steps are as follows.

Preparation of DNA-stable silver nanoclusters: at 0° C., a certain amount of silver nitrate solution and DNA solution are added to 1 mL of double-distilled water, a magnetic stirring is performed for 20 minutes to form a homogeneous mixture, then a freshly prepared sodium borohydride solution is added, and a reaction is carried under a vigorous stirring in a dark place for 20 minutes, wherein molar concentrations of the silver nitrate, the DNA and the sodium borohydride are 5 mmol/L, 200 μmol/L and 5 mmol/L, respectively. The resulting product solution is filtered by a 0.4 μm filter, and a filtrate is dialyzed through a dialysis bag with a molecular weight cut-off of 5000 Daltons to remove unreacted experimental materials, and the solution in the dialysis bag is subjected to a rotary evaporation to remove 90% of the solvent, and then freeze-dried to obtain a dry sample of the silver nanoclusters, and the dry sample of the silver nanoclusters is stored at 4° C. in a dark condition.

Preparation of silver nanocluster-rhodamine 6G complex: the prepared silver nanoclusters are dissolved in 200 μL of double-distilled water, 100 μL of citrate buffer (pH 5.5) is added to mix well, and then 100 μL of rhodamine 6G solution (0.1-0.5 nmol/L) is added. The mixed solution reacts in a dark place for 30 minutes, and the product solution is subjected to centrifugal separation, ethanol washing and vacuum drying to obtain the silver nanocluster-rhodamine 6G complex.

The prepared complex is dispersed in 100 μL of citrate buffer, and the mass concentration of the complex is 1-2 mg/mL. After homogeneous solution of the complex is incubated in a dark place for 30 minutes, fluorescence emission spectra of the homogeneous solution of the complex corresponding to different molar concentrations of rhodamine 6G are measured respectively, and the intensity of double emission fluorescence peak is optimized to determine the ratio of silver nanocluster and rhodamine 6G (see FIG. 2).

At room temperature and under a slow magnetic stirring, 15 μL of melamine solutions with different concentrations are added to the prepared homogeneous solution of complex having the optimized ratio, and the solution is continuously stirred for 5 minutes to fully react to form a homogeneous solution of the complex and the melamine. Fluorescence emission spectra of the homogeneous solution of the complex and melamine corresponding to different molar concentrations of melamine are measured respectively (see FIG. 3). The ratio $F_{DNA\text{-}Ag\ NCs}/F_{Rh\ 6G}$ of fluorescence emission peak intensities of the silver nanocluster to rhodamine 6G and the molar concentration $C_{MA}$ of the melamine are fitted to obtain a linear relationship as $F_{DNA\text{-}Ag\ NCs}/F_{Rh\ 6G}=0.06014 C_{MA}+0.5612$ ($R^2=0.9959$) (see FIG. 4). Therefore, the ratiometric fluorescent probe for melamine can be constructed, wherein the linear concentration of melamine to be detected is 2-10 μmol/L, and the detection limit of melamine is 0.2 μmol/L.

Embodiment 2

The specific process steps for preparing DNA-stable silver nanoclusters in this embodiment are the same as those in embodiment 1, wherein the molar concentrations of silver nitrate, DNA and sodium borohydride are 8 mmol/L, 400 μmol/L and 7 mmol/L, respectively. The prepared silver nanoclusters are dissolved in 200 μL of double-distilled water, 100 μL of citrate buffer (pH 6.0) is added to mix well, and then 100 μL of rhodamine 6G solution (0.2-1 nmol/L) is added. The mixed solution reacts in a dark place for 30 minutes, and the product solution is subjected to centrifugal separation, ethanol washing and vacuum drying to obtain a silver nanocluster-rhodamine 6G complex. The prepared complex is dispersed in 100 μL of citrate buffer, and the mass concentration of the complex is 1-4 mg/mL. After the homogeneous solution of the complex is incubated in a dark place for 30 minutes, fluorescence emission spectra of the homogeneous solution of the complex corresponding to different molar concentrations of rhodamine 6G are measured respectively, and the intensity of double emission fluorescence peak is optimized to determine the ratio of silver nanocluster and rhodamine 6G. At room temperature and under a slow magnetic stirring, 15 μL of melamine solutions with different concentrations are added to the prepared homogeneous solution of complex having the optimized ratio, and the solution is continuously stirred for 5 minutes to fully react to form a homogeneous solution of the complex and the melamine. Fluorescence emission spectra of the homogeneous solution of the complex and melamine corresponding to different molar concentrations of melamine are measured respectively. By fitting a linear relationship between the ratio of fluorescence emission peak intensities of the silver nanocluster to rhodamine 6G and the molar concentration of the melamine, the ratiometric fluorescent probe for melamine can be constructed, wherein the linear concentration of melamine to be detected is 0.5-10 μmol/L, and the detection limit of melamine is 0.05 μmol/L.

Embodiment 3

The specific process steps for preparing DNA-stable silver nanoclusters in this embodiment are the same as those in embodiment 1, wherein the molar concentrations of silver nitrate, DNA and sodium borohydride are 10 mmol/L, 600 μmol/L and 10 mmol/L, respectively. The prepared silver nanoclusters are dissolved in 200 μL of double-distilled water, 100 μL of citrate buffer (pH 6.5) is added to mix well, and then 100 μL of rhodamine 6G solution (0.2-2 nmol/L) is added. The mixed solution reacts in a dark place for 30 minutes, and the product solution is subjected to centrifugal separation, ethanol washing and vacuum drying to obtain a silver nanocluster-rhodamine 6G complex. The prepared complex is dispersed in 100 μL of citrate buffer, and the mass concentration of the complex is 2-5 mg/mL. After the homogeneous solution of the complex is incubated in a dark place for 30 minutes, fluorescence emission spectra of the homogeneous solution of the complex corresponding to different molar concentrations of rhodamine 6G are measured respectively, and the intensity of double emission fluorescence peak is optimized to determine the ratio of silver nanocluster and rhodamine 6G. At room temperature and under a slow magnetic stirring, 15 μL of melamine solutions with different concentrations are added to the prepared homogeneous solution of complex having the optimized ratio, and the solution is continues stirred for 5 minutes to fully react to form a homogeneous solution of the complex and the melamine. Fluorescence emission spectra of the homogeneous solution of the complex and the melamine corresponding to different molar concentrations of melamine are measured respectively. By fitting a linear relationship between the ratio of fluorescence emission peak intensities of the silver nanocluster to rhodamine 6G and the molar concentration of the melamine, the ratiometric fluorescent probe for melamine can be constructed, wherein the linear concentration of melamine to be detected is 2-15 μmol/L, and the detection limit of melamine is 0.1 μmol/L.

Embodiment 4

This embodiment relates to an application of the ratiometric fluorescent probe for melamine prepared in embodiment 1 in detecting melamine in an actual sample such as milk. The milk is mixed with melamine with different concentrations and acetonitrile, and after 30 minutes of ultrasonic treatment, the mixed solution is obtained. The mixed solution is centrifuged for 15 minutes at a speed of 14000 rpm, and the supernatant is taken and filtered. The filtrate is further diluted 25 times and collected for further detection. Specifically, for melamine, the detection range of molar concentration is 0.5-15 μmol/L, the detection limit is 0.09 μmol/L, detection recovery rate is 99.8-100.5%, and relative standard deviation is 1.1-2.1%. Compared with the prior art, the previous literatures (*Talanta*, 2015, 136, 47-53 and *Appl. Surf Sci.*, 2017, 420, 963-969) use single method or ratiometric fluorescence method to detect melamine, and the detection recovery rate of melamine in milk samples is 94.0-102.0%, and the relative standard deviation is 1.2-3.2%. The ratiometric fluorescent probe of the present disclosure has high detection recovery rate, low relative standard deviation, simple preparation process, low cost and high product sensitivity, and can be developed into a novel ratiometric fluorescent probe for melamine, where the novel ratiometric fluorescent probe is suitable for efficiently detecting melamine in different actual samples.

What is claimed is:
1. A method for preparing a ratiometric fluorescent probe for melamine based on a silver nanocluster complex, comprising the following steps:
(1) preparation of DNA-stable silver nanoclusters: at 0° C., adding a predetermined amount of silver nitrate solution and DNA solution to 1 mL of double-distilled water to obtain a first solution, stirring the first solution magnetically for 20 minutes to form a homogeneous mixture, then adding a sodium borohydride solution to the homogeneous mixture to obtain a second solution, and performing a reaction on the second solution under a vigorous stirring in a dark place for 20 minutes to obtain a first product solution; wherein the first product solution is filtered by a 0.4 μm filter to obtain a filtrate, and the filtrate is dialyzed through a dialysis bag with a molecular weight cut-off of 5000 Daltons to remove unreacted experimental materials; a solution in the dialysis bag is subjected to a rotary evaporation to remove 90% of a solvent, and then freeze-dried to obtain a dry sample of the DNA-stable silver nanoclusters; the dry sample of the DNA-stable silver nanoclusters is stored at 4° C. in a dark condition;
(2) preparation of a DNA-stable silver nanocluster-rhodamine 6G complex: dissolving the DNA-stable silver nanoclusters prepared in step (1) in 200 μL of double-distilled water to obtain a third solution, adding 100 μL of citrate buffer to the third solution to mix well to obtain a fourth solution, and then adding 100 μL of rhodamine 6G solutions with different molar concentrations to the fourth solution to obtain a plurality of fifth solutions; wherein each fifth solution of the plurality of fifth solutions reacts in a dark place for 30 minutes to obtain a second product solution, and the second product solution is subjected to centrifugal separation, ethanol washing and vacuum drying to obtain the DNA-stable silver nanocluster-rhodamine 6G complex;

(3) dispersing the DNA-stable silver nanocluster-rhodamine 6G complex prepared in step (2) in 100 μL of citrate buffer to obtain a sixth solution, incubating the sixth solution in a dark place for 30 minutes to obtain a first homogeneous solution, measuring a fluorescence emission spectrum of the first homogeneous solution, optimizing an intensity of a double emission fluorescence peak of the first homogeneous solution to determine a ratio of the DNA-stable silver nanoclusters and the rhodamine 6G to obtain a homogeneous solution having an optimized ratio;

(4) at room temperature and under a slow magnetic stirring, adding 15 μL of melamine solutions with different concentrations to the homogeneous solution having the optimized ratio to obtain a plurality of seventh solutions, continuing to stir the plurality of seventh solutions for 5 minutes to fully react to form a plurality of second homogeneous solutions, measuring fluorescence emission spectra of the plurality of second homogeneous solutions, fitting a linear relationship between a ratio of fluorescence emission peak intensities of the DNA-stable silver nanoclusters to the rhodamine 6G and a molar concentration of the melamine, constructing the ratiometric fluorescent probe for melamine;

wherein in step (1), a size of each of the DNA-stable silver nanoclusters is 6-12 nm, a molar concentration of the silver nitrate solution is 5-10 mmol/L, a molar concentration of the DNA solution is 200-600 mmol/L, and a molar concentration of the sodium borohydride solution is 5-10 mmol/L; in step (2), a pH of the citrate buffer is 5.5-6.5, and a range of the different molar concentrations of the rhodamine 6G is 0.1-2 nmol/L; in step (3), a mass concentration of the sixth solution is 1-5 mg/mL; in step (4), a range of the different concentrations of the melamine solutions is 0.5-15 μmol/L, and a detection limit of the melamine is 0.05-0.2 μmol/L.

* * * * *